US011738120B1

(12) United States Patent
Berrios

(10) Patent No.: US 11,738,120 B1
(45) Date of Patent: Aug. 29, 2023

(54) SYNTHESIS OF TAUROLIDINE, PURITY PROFILES AND POLYMORPHS

(71) Applicant: CorMedix Inc., Berkeley Heights, NJ (US)

(72) Inventor: Reyes M. Berrios, Lyndhurst, NJ (US)

(73) Assignee: CorMedix Inc., Berkeley Heights, NJ (US)

( * ) Notice: Subject to any disclaimer, the term of this patent is extended or adjusted under 35 U.S.C. 154(b) by 0 days.

(21) Appl. No.: 17/721,699

(22) Filed: Apr. 15, 2022

Related U.S. Application Data

(60) Provisional application No. 63/331,050, filed on Apr. 14, 2022.

(51) Int. Cl.
*A61L 29/16* (2006.01)
*A61L 33/00* (2006.01)
*A61K 31/549* (2006.01)

(52) U.S. Cl.
CPC ............ *A61L 29/16* (2013.01); *A61K 31/549* (2013.01); *A61L 33/0011* (2013.01); *A61L 2300/216* (2013.01); *A61L 2300/404* (2013.01)

(58) Field of Classification Search
CPC .... A61L 29/16; A61L 2300/404; A61L 29/14; A61L 2300/42; A61L 2300/216; A61L 2300/21; A61L 2/0088; A61L 2/18; A61L 2202/24; A61L 2300/406; A61L 29/08; A61L 2300/204; A61L 2/186; A61L 2300/206; A61L 2300/214; A61L 29/043; A61L 29/085; A61L 29/106; A61L 29/00; A61L 33/04; A61L 33/06; A61L 29/02; A61L 29/06; A61L 2300/45; A61L 2300/104; A61L 2/16; A61L 29/126; A61L 2/00; A61L 2300/106; A61L 2300/402;
(Continued)

(56) References Cited

U.S. PATENT DOCUMENTS 4,096,241 A 6/1978 Geistlich et al.
4,107,305 A 8/1978 Pfirrmann
(Continued)

FOREIGN PATENT DOCUMENTS

CN 105709214 6/2016
DE 35 33 612 4/1987
(Continued)

OTHER PUBLICATIONS

T.S.J. Elliot and A. Curran, "Effects of Heparin and Chlorbutol on Bacterial Colonisation of Intravascular Cannulae in an In Vitro Model," *Journal of Hospital Infection*, 14(3): pp. 193-200, Oct. 1, 1989. https://www.journalofhospitalinfection.com/article/0195-6701(89)90035-2/pdf#relatedArticles (Abstract Only).
(Continued)

*Primary Examiner* — Audrea B Coniglioz
(74) *Attorney, Agent, or Firm* — DLA Piper LLP (US)

(57) ABSTRACT

Improved methods for synthesizing taurolidine, improved compositions or formulations comprising taurolidine and methods for reducing an amount of impurities in taurolidine are provided herein, among other things. The taurolidine may be substantially free of impurities. The taurolidine may be a polymorph, for example, Polymorph A or Polymorph B. The composition or formulation may comprise Low-Molecular-Weight (LMW) Heparin.

24 Claims, 5 Drawing Sheets

XRPD Taurolidine Polymorph A

(58) Field of Classification Search
CPC .... A61L 33/0041; A61L 33/068; A61L 33/00; A61L 33/0011; A61L 2/232; A61L 31/16; A61L 15/46; A61L 17/005; A61L 2202/21; A61L 33/0005; A61L 15/44; A61L 27/54; A61L 29/143; A61L 2420/06; A61L 2300/11; A61L 2300/232; A61L 2300/408; A61L 2300/418; A61L 2300/442; A61L 2400/04; A61L 26/0028; A61L 26/0066; A61L 26/008; A61L 29/005; A61L 33/18; A61L 2300/114; A61L 2300/60; A61L 2420/02; A61L 27/36; A61L 15/22; A61L 17/04; A61L 17/08; A61L 17/10; A61L 17/105; A61L 17/12; A61L 2300/102; A61L 2300/20; A61L 2300/802; A61L 33/02; A61L 31/10; A61L 2420/08; A61L 2300/416; A61L 2300/608; A61L 2300/63; A61L 2300/602; A61L 27/34; A61L 17/145; A61L 2300/426; A61L 27/50; A61L 29/148; A61L 31/08; A61L 31/14; A61L 31/148; A61L 27/16; A61L 2300/606; A61M 2025/0019; A61M 2025/0056; A61M 25/0017; A61M 39/20; A61M 39/16; A61M 25/00; A61M 39/162; A61M 5/31511; A61M 39/02; A61M 1/3661; A61M 2005/3104; A61M 2039/1033; A61M 2005/31506; A61M 5/002; A61M 5/3135; A61M 5/347; A61M 5/3137; A61M 60/13; A61M 60/414; A61M 60/833; A61M 2210/12; A61M 2202/0405; A61M 60/585; A61M 5/001; A61M 2025/0031; A61M 2205/3303; A61M 2039/0258; A61M 2230/30; A61M 60/237; A61M 25/003; A61M 39/18; A61M 2209/10; A61M 25/0075; A61M 5/31513; A61M 25/04; A61M 5/31; A61M 2205/32; A61M 2205/33; A61M 60/148; A61M 60/242; A61M 60/31; A61M 60/508; A61M 60/861; A61M 2205/8206; A61M 1/00; A61M 1/169; A61M 2025/1015; A61M 2025/1022; A61M 2025/1052; A61M 2025/1097; A61M 2205/3317; A61M 2205/3344; A61M 25/0045; A61M 25/10184; A61M 27/002; A61M 60/523; A61M 60/531; A61M 60/806; A61M 60/865; A61M 1/3653; A61M 1/3659; A61M 25/007; A61M 2025/0034; A61M 2025/0073; A61M 2209/06; A61M 25/0043; A61M 39/0247; A61M 39/22; A61M 5/315; A61M 60/135; A61M 1/3655; A61M 2207/00; A61M 5/007; A61M 1/285; A61M 2039/027; A61M 2039/0285; A61M 2039/0291; A61M 2205/3379; A61M 2250/00; A61M 25/0074; A61M 1/1682; A61M 2025/0076; A61M 2025/0078; A61M 2025/0037; A61M 2025/105; A61M 2205/3306; A61M 2205/3331; A61M 2210/0693; A61M 2210/1082; A61M 2210/1089; A61M 2230/06; A61M 2230/42; A61M 2230/63; A61M 25/0068; A61M 25/0108; A61M 25/1011; A61M 3/0262; A61M 3/0283; A61M 60/279; A61M 60/30; A61M 60/50; A61M 25/0097; A61M 25/01; A61M 1/3656; A61M 2025/0018; A61M 2039/0288; A61M 2039/0294; A61M 2205/0205; A61M 2205/582; A61M 25/0105; A61M 25/0111; A61M 39/0208; A61M 39/165; A61M 5/178; A61M 2025/0057; A61M 25/0029; A61M 25/0194; A61M 5/14; A61M 2005/1403; A61M 2039/0018; A61M 2039/0273; A61M 2039/064; A61M 2039/2426; A61M 2205/0216; A61M 2205/583; A61M 2210/125; A61M 25/001; A61M 25/0071; A61M 39/06; A61M 5/427; A61M 60/205; A61M 60/40; A61M 2005/14284; A61M 2005/1587; A61M 2025/0063; A61M 2039/0202; A61M 2039/0205; A61M 2039/0241; A61M 2202/0275; A61M 2205/04; A61M 5/158; A61M 1/024; A61M 1/16; A61M 1/3496; A61M 1/3679; A61M 2005/3103; A61M 2005/342; A61M 2025/0006; A61M 2039/263; A61M 2202/0413; A61M 2202/0478; A61M 2205/50; A61M 2205/52; A61M 25/0009; A61M 25/0069; A61M 27/008; A61M 39/10; A61M 39/26; A61M 5/1424; A61M 5/19; A61M 60/216; A61M 1/3687; A61M 2005/1401; A61M 2005/1402; A61M 2005/31523; A61M 2025/0079; A61M 2025/0096; A61M 2025/091; A61M 2039/167; A61M 2039/2433; A61M 2205/05; A61M 25/0082; A61M 25/0102; A61M 39/00; A61M 39/105; A61M 5/1409; A61M 5/2448; A61M 5/31596; A61M 5/50; A61K 31/18; A61K 2300/00; A61K 45/06; A61K 9/0019; A61K 47/12; A61K 9/08; A61K 31/5377; A61K 31/222; A61K 31/24; A61K 31/255; A61K 31/341; A61K 31/343; A61K 31/381; A61K 31/404; A61K 31/42; A61K 31/433; A61K 31/4436; A61K 31/538; A61K 47/40; A61K 31/727; A61K 47/32; A61K 47/10; A61K 31/198; A61K 31/045; A61K 31/20; A61K 31/185; A61K 47/34; A61K 31/155; A61K 31/135; A61K 31/205; A61K 31/496; A61K 31/60; A61K 31/612; A61K 33/38; A61K 31/549; A61K 33/40; A61K 47/24; A61K 9/0014; A61K 31/194; A61K 31/21; A61K 38/38; A61K 31/167; A61K 31/245; A61K 31/445; A61K 31/47; A61K 47/36; A61K 31/19; A61K 33/42; A61K 38/00; A61K 2800/74; A61K 31/16; A61K 31/201; A61K 31/685; A61K 31/715; A61K 38/49; A61K 8/06; A61K 8/361; A61K 8/553; A61K 9/107; A61K 31/095; A61K 38/06; A61K 38/07; A61K 31/40; A61K 31/4174; A61K 31/10; A61K 31/145; A61K 31/191; A61K 31/327; A61K 31/7004; A61K 31/732; A61K 47/20; A61K 31/675; A61K 38/34; A61K 47/00; A61K 47/18; A61K 47/183; A61K 47/26; A61K 47/6803; A61K 47/6809; A61K 47/6855;

A61K 9/19; A61K 31/202; A61K 31/505;
A61K 31/5415; A61K 31/65; A61K
47/28; A61K 38/05; A61K 47/60; A61K
31/085; A61K 31/4985; A61K 31/722;
A61K 31/728; A61K 33/06; A61K 38/04;
A61K 38/39; A61K 9/0004; A61K 9/06;
A61K 9/5146; A61K 2039/505; A61K
31/132; A61K 31/133; A61K 31/195;
A61K 31/29; A61K 31/315; A61K
31/663; A61K 335/16; A61K 39/395;
A61K 39/39558; A61K 47/50; A61K
47/6957; A61K 9/5153; A61K 31/047;
A61K 31/165; A61K 31/22; A61K
31/403; A61K 31/437; A61K 31/454;
A61K 31/4745; A61K 31/475; A61K
31/513; A61K 31/555; A61K 31/7076;
A61K 33/14; A61K 33/243; A61K 35/00;
A61K 38/1833; A61K 48/0066; A61K
49/0004; A61K 49/0008; A61K 49/006;
A61K 9/14; A61K 9/5123; A61K 31/428;
A61K 31/5375; A61K 9/20; A61K
9/2054; A61K 9/2059; A61K 9/2866;
A61K 31/485; A61K 47/38; A61K
9/0056; A61K 9/006; A61K 9/1635;
A61K 9/1652; A61P 31/04; A61P 7/02;
A61P 31/00; A61P 9/04; A61P 9/00;
A61P 35/00; A61P 17/00; A61P 25/00;
A61P 13/12; A61P 23/00; A61P 31/10;
A61P 31/22; A61P 31/02; A61P 11/00;
A61P 23/02; A61P 25/28; A61P 1/16;
A61P 43/00; A61P 31/12; A61P 3/10;
A61P 9/10; A61P 27/02; A61P 41/00;
A61P 17/02; A61P 25/20; A61P 5/38;
A61P 37/02; A61P 29/00; A61P 31/14;
A61P 31/20; A61P 33/00; A61P 33/10;
A61P 33/14; A61P 37/06; A61P 7/08;
A61P 25/36; A61P 25/16; A61P 15/00;
A61P 19/00; A61P 25/02; A61P 35/02;
A61P 5/00; A61P 1/04; A61P 1/18; A61P
13/08; A61P 13/10; A61P 21/00; A61P
37/04; A61P 39/00; A61P 1/00; A61P
1/02; A61P 11/06; A61P 13/00; A61P
13/02; A61P 15/02; A61P 19/10; A61P
25/04; A61P 25/14; A61P 25/18; A61P
25/24; A61P 27/06; A61P 3/00; A61P
3/04; A61P 3/06; A61P 31/18; A61P
39/02; A61P 5/50; A61P 7/00; A61P 7/06;
A61P 9/02; A61P 25/30; A61P 25/08;
A61P 25/22; A61P 25/26; A61P 19/02;
A61P 19/04; A61P 25/06

See application file for complete search history.

(56) References Cited

U.S. PATENT DOCUMENTS

| | | |
|---|---|---|
| 4,337,251 A | 6/1982 | Pfirrmann |
| 4,587,268 A | 5/1986 | Pfirrmann |
| 4,587,284 A | 5/1986 | Lüissi et al. |
| 4,604,391 A | 8/1986 | Pfirrmann |
| 4,626,536 A | 12/1986 | Pfirrmann |
| 4,654,338 A | 3/1987 | Jones et al. |
| 4,772,468 A | 9/1988 | Pfirrmann |
| 4,797,282 A | 1/1989 | Wahlig et al. |
| 4,853,225 A | 8/1989 | Wahlig et al. |
| 4,882,149 A | 11/1989 | Spector et al. |
| 4,905,700 A | 3/1990 | Wokalek et al. |
| 4,960,415 A | 10/1990 | Reinmüller |
| 4,980,374 A | 12/1990 | Steudle et al. |
| 5,032,615 A | 7/1991 | Ward et al. |
| 5,077,281 A | 12/1991 | Reinmüller |
| 5,167,961 A | 12/1992 | Lussi et al. |
| 5,210,083 A | 5/1993 | Pfirrmann |
| 5,362,754 A | 11/1994 | Raad et al. |
| 5,417,675 A | 5/1995 | Watanabe et al. |
| 5,417,975 A | 5/1995 | Lussi et al. |
| 5,573,771 A | 11/1996 | Geistlich et al. |
| 5,593,665 A | 1/1997 | Pfirrmann et al. |
| 5,603,921 A | 2/1997 | Bowen |
| 5,688,516 A | 11/1997 | Raad et al. |
| 5,725,553 A | 3/1998 | Moenning |
| 5,889,183 A | 3/1999 | Herdeis et al. |
| 5,899,874 A | 5/1999 | Jonsson |
| 5,954,691 A | 9/1999 | Prosl |
| 6,011,030 A | 1/2000 | Pfirrmann |
| 6,166,007 A | 12/2000 | Sodemann |
| 6,174,537 B1 | 1/2001 | Khan |
| 6,258,797 B1 | 7/2001 | Lehner |
| 6,350,251 B1* | 2/2002 | Prosl ............... A61L 29/16 604/93.01 |
| 6,423,706 B2 | 7/2002 | Sodemann |
| 6,447,488 B2 | 9/2002 | Estabrook et al. |
| 6,479,481 B1 | 11/2002 | Stendel et al. |
| 6,498,157 B2 | 12/2002 | Sodemann |
| 6,569,852 B1 | 5/2003 | Sodemann |
| 6,592,564 B2 | 7/2003 | Finch et al. |
| 6,679,870 B1 | 1/2004 | Finch et al. |
| 6,685,694 B2* | 2/2004 | Finch ............... A61L 29/16 604/93.01 |
| 6,753,328 B2 | 6/2004 | Wands et al. |
| 6,821,968 B2 | 11/2004 | Pfirrmann |
| 7,122,541 B2 | 10/2006 | Wands et al. |
| 7,132,413 B1 | 11/2006 | Pfirrmann |
| 7,601,731 B2 | 10/2009 | Raad |
| 7,696,182 B2* | 4/2010 | Prosl ............... A61K 31/185 514/56 |
| 7,833,215 B2 | 11/2010 | Appling |
| 7,977,403 B2 | 7/2011 | Lohrmann et al. |
| 8,236,794 B2 | 8/2012 | Pfirrmann |
| 8,541,393 B2* | 9/2013 | Prosl ............... A61L 29/16 514/56 |
| 8,691,286 B2 | 4/2014 | Gupta et al. |
| 8,747,911 B2 | 6/2014 | Gupta et al. |
| 8,952,148 B2 | 2/2015 | Pullagurla et al. |
| 9,072,868 B2 | 7/2015 | Ziebol et al. |
| 9,339,036 B2* | 5/2016 | Prosl ............... A61L 29/16 |
| 9,649,411 B2 | 5/2017 | Hoang |
| 9,700,676 B2 | 7/2017 | Anderson et al. |
| 9,750,927 B2 | 9/2017 | Ma |
| 9,789,280 B2 | 10/2017 | Ma |
| 9,872,941 B2 | 1/2018 | Hoang |
| 10,300,176 B2 | 5/2019 | Woo et al. |
| 10,507,269 B2 | 12/2019 | Woo et al. |
| 11,389,634 B2 | 7/2022 | Ziebol et al. |
| 2002/0091123 A1 | 7/2002 | Redmond et al. |
| 2003/0225066 A1 | 10/2003 | Polaschegg |
| 2004/0156908 A1 | 8/2004 | Polaschegg |
| 2010/0031277 A1 | 12/2010 | Prosl |
| 2010/0331277 A1* | 12/2010 | Prosl ............... A61L 29/043 514/56 |
| 2015/0148287 A1 | 5/2015 | Woo et al. |

FOREIGN PATENT DOCUMENTS

| | | |
|---|---|---|
| DE | 41 37 544 | 5/1993 |
| EP | 0 244 834 | 3/1992 |
| EP | 0 698 398 | 2/1996 |
| EP | 0 863 133 | 9/2001 |
| EP | 1 245 247 | 10/2002 |
| EP | 1 327 453 | 7/2003 |
| EP | 1 089 738 | 5/2006 |
| EP | 0 946 221 | 8/2006 |
| EP | 1 035 855 | 7/2007 |
| EP | 1 814 562 | 1/2014 |
| EP | 2 742 945 | 6/2014 |
| EP | 2 643 308 | 8/2016 |

(56) References Cited

FOREIGN PATENT DOCUMENTS

| ES | 2031849 | 1/1993 |
|---|---|---|
| GB | 1 124 285 | 8/1968 |
| JP | 63-500943 | 4/1988 |
| WO | 86/01415 | 3/1968 |
| WO | 94/03174 | 2/1994 |
| WO | 97/25052 | 7/1997 |
| WO | 98/28027 | 7/1998 |
| WO | 00/01391 | 1/2000 |
| WO | 00/10385 | 3/2000 |
| WO | 01/52926 | 7/2001 |
| WO | 2006/049813 | 5/2006 |
| WO | 2006/050161 | 5/2006 |
| WO | 2012/070066 | 5/2012 |
| WO | 2015/077798 | 5/2015 |
| WO | 2017/154015 | 9/2017 |

OTHER PUBLICATIONS

Cowan, RN, MSN, OCN, Catherine E., "Antibiotic Lock Technique," *Journal of Intravenous Nursing*, 15(5): pp. 283-287, Sep.-Dec. 1992. https://pubmed.ncbi.nlm.nih.gov/1487784/.

Mochizuki, Manabu et al., "Modification of Central Venous Catheter Flush Solution Improves In Vitro Antimicrobial Activity," *Journal of Infectious Diseases*, 166(4): pp. 994-996, Oct. 1992.

"Preliminary Results Treating Persistent Central Venous Catheter Infections with the Antibiotic Lock Technique in Pediatric Patients," *The Pediatric Infectious Disease Journal*, 13(10): pp. 930-931, Oct. 1994.

Alton, Michael, "Prophylaxis against Dialysis Catheter-Related Bacteremia with a Novel Antimicrobial Lock Solution," *Clinical Infectious Diseases*, 36, pp. 1539-1544, Jun. 15, 2003.

"ASAIO Renal Abstract," *ASAIO Journal*, 55(2): p. 178, Mar.-Apr. 2009, https://journals.lww.com/asaiojournal/toc/2009/03000, 2009.

Betjes, Michiel G.H. et al., "Prevention of dialysis catheter-related sepsis with a citrate-taurolidine-containing lock solution," *Nephrology Dialysis Transplantation*, 19(6): pp. 1-6, Feb. 19, 2004, https://academic.oup.com/ndt/article/19/6/1546/1857203.

Macrae, Jennifer M. et al., "Citrate 4% versus Heparin and the Reduction of Thrombosis Study (CHARTS)," *Clinical Journal of the American Society of Nephrology*, 3(2): pp. 369-374, Mar. 2008. https://cjasn.asnjournals.org/content/3/2/369.

Nori, Uday S. et al., "Comparison of Low-Dose Gentamicin with Minocycline as Catheter Lock Solutions in the Prevention of Catheter-Related Bacteremia," *American Journal of Kidney Diseases*, 48(4): pp. 596-605, Oct. 2006, https://pubmed.ncbi.nlm.nih.gov/16997056/.

Polaschegg, Hans-Dietrich, "Loss of Catheter locking Solution Caused by Fluid Density," *ASAIO Journal*, 51(3): pp. 230-235, May-Jun. 2005, https://journals.lww.com/asaiojournal/Fulltext/2005/05000/Loss_of_Catheter_Locking_Solution_Caused_by_Fluid.9.aspx.

Spektrum Der Dialyse & Apherese, Brochure, Aug. 2014, English Translation, https://docplayer.org/54273708-Spektrum-der-dialyse-apherese-i-04-2014.html.

Quarello, Francesco et al., "Prevention of Hemodialysis Catheter-Related Bloodstream Infection Using an Antimicrobial Lock," *Blood Purification*, 20: pp. 87-92, Jan. 17, 2002, Abstract Only, https://pubmed.ncbi.nlm.nih.gov/11803164/.

Taylor, Caroline, et al., "A New Haemodialysis Catheter-Locking Agent Reduces Infections in Haemodialysis Patients," *Journal of Renal Care*, 34(3): pp. 116-120, Sep. 2008, https://pubmed.ncbi.nlm.nih.gov/18786077/, Abstract Only.

Weijmer, Marcel C., et al., "Randomized, Clinical Trial Comparison of Trisodium Citrate 30% and Heparin as Catheter-Locking Solution in Hemodialysis Patients," *Journal of the American Society of Nephrology*, 16(9): pp. 2769-2777, Sep. 2005, https://jasn.asnjournals.org/content/16/9/2769.

Yevzlin, Alexander S., et al., "Concentrated Heparin Lock is Associated with Major Bleeding Complications after Tunneled Hemodialysis Catheter Placement," *Seminars in Dialysis*, 20(4): pp. 351-354, Jul.-Aug. 2007, https://pubmed.ncbi.nlm.nih.gov/17635828/, Abstract Only.

"ASAIO Renal Abstract," *ASAIO Journal*, 55(2): pp. 177-178, Mar.-Apr. 2009, https://journals.lww.com/asaiojournal/Citation/2009/03000/ASAIO_Renal_Abstracts.3.aspx.

Moran, J.E., et al., "Locking Solutions for Hemodialysis Catheters; Heparin and Citrate—A Position Paper by ASDIN," *Seminars in Dialysis*, 21(5): pp. 1-3, Oct. 2, 2008, https://onlinelibrary.wiley.com/doi/10.1111/j.1S25-139X 2008.00466 x, Abstract Only.

Braumann, C., et al., "Influence of intaperitoneal and systemic application of taurolidine and taurolidine/heparin during laparoscopy on Intraperitoneal and subcutaneous tumour growth in rats," *Clinical & Experimental Metastasis*, 18: pp. 547-552, Nov. 2000. https://link.springer.com/article/10.1023/A:1011988923523, Abstract Only.

McIntyre et al., "Locking of tunneled hemodialysis catheters with gentamicin and heparin," Kidney International, 66(2): pp. 801-805, Aug. 1, 2004, https://www.kidney-international.org/article/S0085-2538(15)50111-7/fulltext.

Alton, Michael, "Prophylaxis Against Dialysis Catheter-Related Bacteremia: A Glimmer of Hope," *American Journal of Kidney Diseases*, 51(2): pp. 165-168, Feb. 2008, https://www.aikd.org/action/showPDf?pd=80272-638682901602-2.

Beathard, Gerald A. et al., "Infection Associated with Tunneled Hemodialysis Catheters," *Seminars in Dialysis*, 21(6): pp. 528-538, Dec. 1, 2008, https://onlinelibrary.wiley.com/doi/epdf/10.1111/j.1525-139X.2008.00497.x.

Droste, Jan C., et al., "Stability and in-vitro efficacy of antibiotic-heparin lock solutions potentially useful for treatment of central venous catheter-related sepsis," *Journal of Antimicrobial Chemotherapy*, 51: pp. 849-855, Mar. 13, 2003, https://pubmed.ncbi.nlm.nih.gov/12654743/.

Jurewitsch, Brian, et al., "Taurolidine 2% as an Antimicrobial Lock Solution for Prevention of Recurrent Catheter-Related Bloodstream Infections," *Journal of Parenteral and Enteral Nutrition*, 22(4): pp. 242-244, Jul. 1, 1998, https://pubmed.ncbi.nih.gov/9661127/, Abstract Only.

Polaschegg, Hans-Dietrich, et al., "Overspill of Catheter locking Solution: Safety and Efficacy" *ASAIO Journal*, 9(6): pp. 713-715,. Nov. 2003, https://journals.lww.com/asailjournal/Fulltext/2003/11000/Overspill_of_Catheter_Locking_Solution_Safety_and.19.aspx.

Root, Jennifer L. et al., "Inhibitory Effect of Disodium EDTA upon the Growth of *Staphylococcus epidermis* In Vitro: Relation to Infection Prophylaxis of Hickman Catheters," *Antimicrobial Agents and Chemotherapy*, 32(11): pp. 1627-1631 Nov. 1988 https://journals.asm.org/doi/cpdf/10.1128/AAC32.11.1627.

Simon, Arnic et al., "Taurolidine-citrate lock solution (TauroLock) significantly reduces CVAD-associated grampositive infections in pediatric cancer patients," *BMC Infectious Diseases*, 8(102): pp. 1-8, Jul. 29, 2008, https://bmcinfectdis.biomedcentral.com/track/pdf/10.1186/1471-2334-8-102.pdf.

Sodemann, Klaus et al., "Two Years' Experience with Dialock and CLS (A New Antimicrobial Lock Solution)," *Blood Purification*, 19(2): pp. 251-254, Feb. 2001, https://www.karger.com/Article/Abstract/46950, Abstract Only.

Blenkham, J.I., "The Antimicrobial Activity of Taurolin—A possible Additive for Parenteral Nutrition Solutions," *Clinical Nutrition*, 6(1): pp. 35-38, Feb. 1, 1987, https://www.clinicalnutritionjournal.com/article/0261-5614 (87) 90066-5/fulltext, Abstract Only.

Darouiche, Rabih O. et al., "Prevention of Catheter-Related Infections: The Skin," *Nutrition*, 13(4):pp. 265-295, Apr. 1997, https://www.sciencedirect.com/science/article/abs/pii/S0899900797002190?via%Dihub, Abstract Only.

Flanigan, Michael J. et al., "Regional Hemodialysis Anticoagulation: Hypertonic Tri-Sodium Citrate or Anticoagulant Citrate Dextrose-A," *American Journal of Kidney Diseases*, 27(4): pp. 519-524, Apr. 1, 1996, https://www.aikd.org/article/S0272-6386 (96) 90162-6.pdf, Abstract Only.

German, S.P. et al., "A Comparative Study of the Microbial Anti-Adherence Capacities of Three Antimicrobial Agents," *Journal of Clinical Pharmacy and Therapeutics*, 12(6): pp. 393-399, Dec. 1987, https://pubmed.ncbi.nlm.nih.gov/3326886/, Abstract Only.

(56) References Cited

OTHER PUBLICATIONS

Johnston, D.A. et al., "Taurolin for the prevention of parenteral nutrition related infection: antimicrobial activity and long-term use,"*Clinical Nutrition*, 12(6): pp. 365-368, Dec. 1993, https://pubmed.ncbi.nlm.nih.gov/16843340/, Abstract Only.
Jones D.S. et al., "The effects of three non-antibiotic antimicrobial agents on the surface hydrophobicity of certain micro-organisms evaluated by different methods," *Journal of Applied Bacteriology*, 71(3): pp. 218-227, Sep. 1991, https://pubmed.ncbi.nlm.nih.gov/1955416/, Abstract Only.
Myers, Evelyn et al., "The Relationship Between Structure and Activity of Taurolin," *Journal of Applied Bacteriology*, 48(1): pp. 89-96 Feb. 1980, https://sfamjournals.onlinelibrary.wiley.com/doi/10.1111/i.1365-2672.1980.tb05210.x, Abstract Only.
Traub, Walter H. et al., "Taurolidine; in vitro Activity against Multiple-Antibiotic-Resistant, Nosocomially Significant Clinical Isolates of *Staphylococcus aureus*, Enterococcus faecium, and Diverse Enterobacteriaceae," *Chemotherapy*, 39(5): pp. 322-330, Sep.-Oct. 1993, https://pubmed.ncbi.nlm.nih.gov/8370323, Abstract Only.
Wanten, G.J. et al., "Taurolidine Versus Heparin Lock to Prevent catheter-Related Bloodstream Infections (CRBSI) in Patients on Home Parenteral Nutrition: A Prospective Randomized Trial," *Clinical Nutrition Supplements*, 3(1): p. 16, 2008, https://cdr.ymaws.com/oley.org/msource/resmgr/Presentations_for_web/Wanten_Abstract.pdf, Abstract Only.
Willatts, Sheila M. et al., "Effect of the antiendotoxic agent, taurolidine, in the treatment of sepsis syndrome: A placebo-controlled, double-blind trial," *Critical Care Medicine*, 23(6): pp. 1033-1039, Jun. 1995, Abstract Only. https://journals.lww.com/ccmjournal/Abstract/1995/06000/Effect_of_the_antiendotoxic_agent,_taurolidine,_in.7.aspx.
Kirsch, Lee E. et al., "The Effect of Polyvinylpyrrolidine on the Stability of Taurolidine," *Pharmaceutical Development and Technology*, 2(4): pp. 345-356, Apr. 25, 1997, https://www.tandfonline.com/doi/abs/10.3109/10837459709022263.3.
European Patent Office, Board of Appeals Decision, Oct. 27, 2010.
Biolink, Neutrolin Declaration of Release "Fieigabeerklärung") Feb. 18, 2003.
Bio-Implant Handels GMBH, Delivery Note ("Lieferschein"), Jun. 24, 2004.
Bio-Implant Handels GMBH, Delivery Note ("Lieferschein"), Jul. 15, 2004.
Nefro-Ion, Delivery Note ("Lieferschein"), Jun. 24, 2004.
Tauropharm GMBH, TauroLock Instructions for Use Apr. 30, 2004.
Tauropharm GMBH, TauroLock Instructions for Use, 2014.
Movianto, Declaration of Release, Sep. 16, 2014.
Asset Purchase Agreement (Redacted), May 12, 2004.
Bill of Sale and Assignment, Jun. 30, 2004.
Heparine Sodique Dakota, Instructions for Use, Jul. 2003.
Taurolok Sanalog, release protocol, Jun. 18, 2004.
Glückauf Apotheke, Delivery Note, Jul. 22, 2004.
Biolink, Addendum Instructions for Use Neutrolin, 2003.
E-mail from Weis Christian to Gregor Weidmann, Taurolock, Jun. 4, 2004.
Gröschner, Georges, Affidavit, Jan. 27, 2015.
Weidmann, Grego, Affidavit, Feb. 2, 2015.
Emails regarding Biolink Norwegian IFU, Jan. 21, 2015.
Declaration of C. Robert Valeri, M.D. Under 37 CFR 1.132, Aug. 14, 2009.
Emails from Prof. Dr. Claus Herdeis, Jan. 21, 2015.
Decision LG Mannheim in re 7 O 2/15, May 8, 2015.
Decision LG Mannheim in re 7 O 118/14. May 8, 2015.
European Patent Office, Preliminary Opinion Opposition Division, May 22, 2015.
Tauropharm GMBH, Writ by TauroPharm in Utility model cancellation, Mar. 5, 2015.
Biolink, Confidentiality Agreements, Mar. 23, 2000.
ND Partners, LLC, Supplemental Data, Sep. 25, 2015.
European Patent Office, Provision of the minutes in accordance with Rule 124(4) EPC, Dec. 22, 2015.
ND Partners, LLC, Declaration of Professor Michael Allon, MD, Opposition Proceeding, Sep. 25, 2015.
Affidavit of Daniel P. Daetwyler, Oct. 17, 2015.
Declaration of Prof. Dr. Claus Herdeis, Oct. 23, 2015.
Street Report, Healthcare Company Update: CorMedix Inc (NYSEMKT:CRMD), Jul. 19, 2015.
Protocol of Utility Model Cancellation proceedings in re DE 20 2005 022 124.4, Jul. 1, 2016.
Correction of protocol of Utility Model Cancellation proceedings in re DE 20 2005 022 124.4, Aug. 31, 2016.
Reasoned Decision of Utility Model Division in re DE 20 2005 022 124.4, Aug. 11, 2016.
Polaschegg, HD, Physics of Catheter Locking Solutions, Dialysis Times, 2005, pp. 1-6.
Biolink, Neutrolin Instructions for Use (Swedish, Finnish, Norwegian), (corresponds to Biolink, IFU, Neutrolin-commercial-#1510, Revision History, last amended Sep. 16, 2002.).
Biolink, IFU, Neutrolin-commercial-#1510, Revision History, last amended Sep. 16, 2002.

* cited by examiner

XRPD Taurolidine Polymorph A

XRPD Taurolidine Polymorph B

FIGURE 4A
XRPD Taurolidine Polymorph A and B
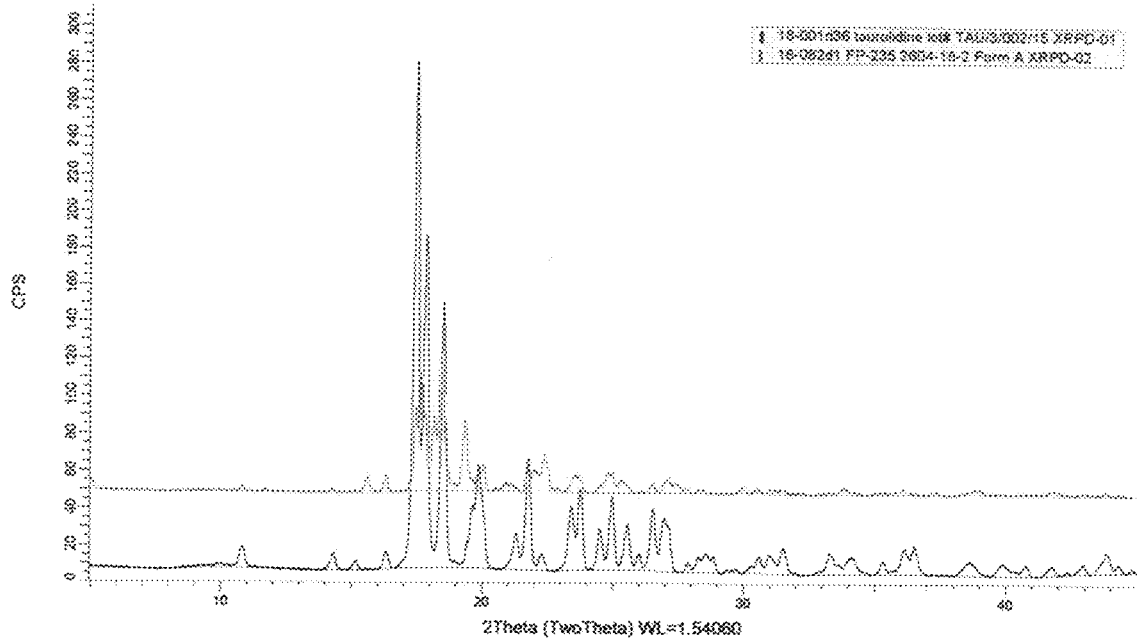
Figure 7: XRPD patterns of sample Taurolidine lot# TAU/3/002/15 (black, bottom) and the reference of Form A, FP-235-2604-18-2 (red, top)
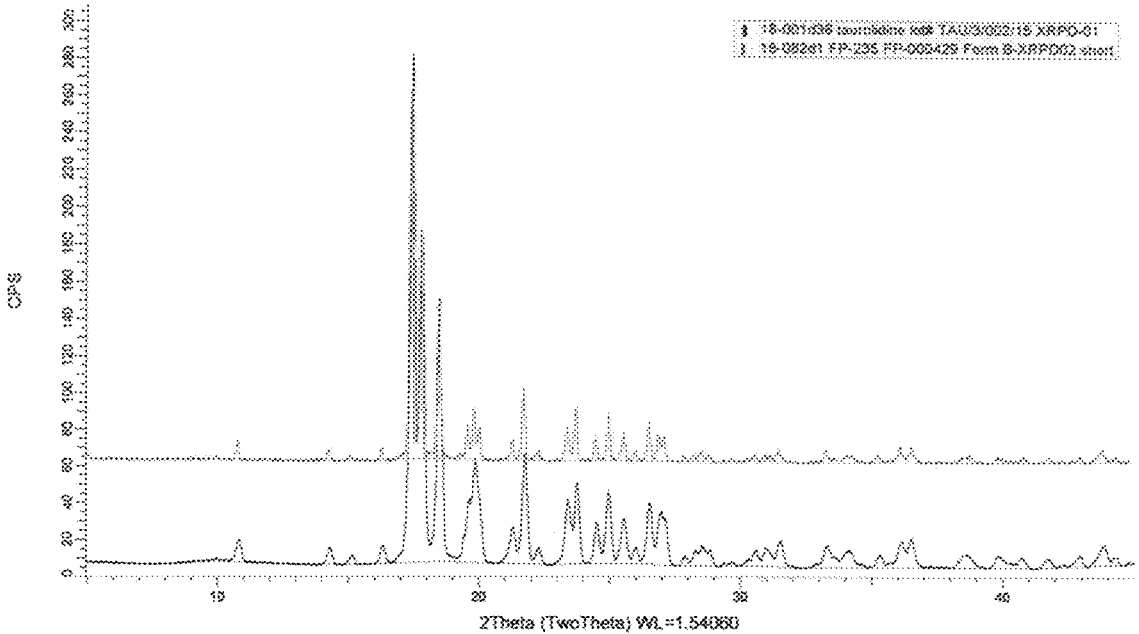
Figure 8: XRPD patterns of sample Taurolidine lot# TAU/3/002/15 (black, bottom) and the reference of Form B, FP-235 FP-000429 (red, top)
FIGURE 4B

SYNTHESIS OF TAUROLIDINE, PURITY PROFILES AND POLYMORPHS

FIELD OF DISCLOSURE

The present disclosure relates to improved taurolidine compositions having improved purity profiles, including pharmaceutical compositions, methods of making and using the same, taurolidine polymorphs, and the synthesis of such taurolidine polymorphs.

BACKGROUND

Hemodialysis access systems for access to a patient's vascular system for exchange of blood between the vascular system and an external processing apparatus are well known in the art. The simplest such system is a catheter alone placed directly in the patient's right jugular vein with the distal end extending into the central venous system, typically into the superior vena cava. Other more complicated systems, for example ports, usually involve indwelling catheters as well. The exchange of blood for hemodialysis treatment typically involves high blood flow rates under conditions designed not to induce shear stress beyond a certain level so as to not cause red cell damage or the activation of platelets.

As with any implanted device, placement of an object that must remain in the patient over a protracted period of time gives rise to the likelihood of blood stream infection promoted by the indwelling device. Infection risk is seriously aggravated by the fact that such devices are frequently handled and manipulated by medical workers, leading to microbial colonization of the catheter's internal surfaces, that is, formation of a biofilm in the lumen. Infection from a biofilm reservoir is much more serious than a simple infection since it is often impossible to eradicate with conventional means. In refractory cases the device must be explanted to treat the patient effectively. As a result, the literature, both scientific and patent, is replete with hopeful but not definitive suggestions as to how to defeat, or at least hold at bay, catheter related infections.

Antibiotics have been used to treat devices such as catheters to prevent infection, but chronic use of antibiotics as a prophylactic accelerates emergence of antibiotic-resistant bacterial strains. Advances in catheter locks described in the scientific literature and other patent documents have involved the use of a substance generally referred to as taurolidine and/or taurinamide and taurinamide derivatives for routine antimicrobial use, in particular in catheters. taurolidine and related compounds are biocidal but are known not to induce development of resistant bacterial strains. For example, Sodemann, U.S. Pat. No. 6,166,007, issued Dec. 26, 2000 and Sodemann, U.S. Pat. No. 6,423,706, issued Jul. 23, 2002, among others, disclosed use of taurolidine and other taurinamide-related compounds as part of a catheter lock solution.

Coagulation of the blood inside catheters in or connected to the vascular system has also proven troublesome and many methods have been tried for its prevention, particularly for inhibiting the clogging of the catheter, which can diminish or destroy the catheter's usefulness. It is standard procedure to flush blood from the catheters and then lock them with a heavy-duty anticoagulant, heparin locking solution being the standard. Unfortunately, heparin alone lacks biocidal capability, but this deficiency is often ignored.

A formulation of taurolidine with citrate and citric acid described in U.S. Pat. Nos. 6,166,007 and 6,423,706, the contents of which are hereby incorporated by reference in their entirety, has worked well in minimizing catheter-caused infections in hemodialysis patients.

However, catheter lock solutions including taurolidine prepared using conventional techniques may include potential impurities remnant from the synthesis of such taurolidine. What is needed is an improved synthesis of taurolidine presenting an improved purity profile and useful compositions including the same.

SUMMARY

The present disclosure provides a method of synthesizing taurolidine. The method may comprise the following steps:

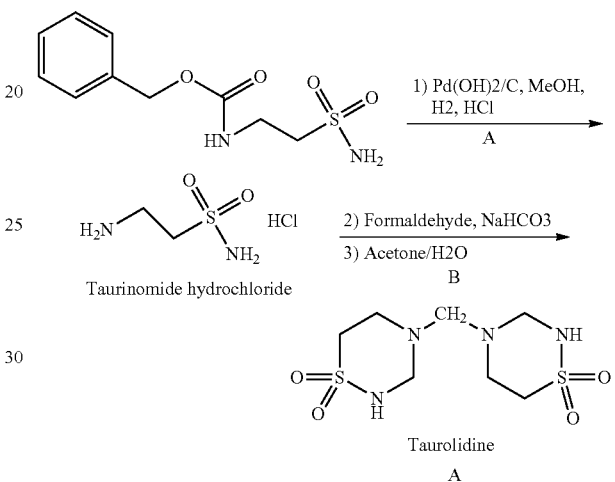

The present disclosure provides a composition or formulation comprising taurolidine, wherein the taurolidine may be substantially free of impurities. The composition or formulation may comprise Low-Molecular-Weight (LMWH) Heparin. A method for reducing an amount of impurities in taurolidine is provided. The method may comprise synthesizing the taurolidine according to the above synthesis.

The taurolidine may be substantially free of impurities. The taurolidine may be a polymorph, for example, Polymorph A as demonstrated by an X-ray powder diffraction (XRPD) in FIG. 2 or Polymorph B as demonstrated by an XRPD in FIG. 3. The polymorphs A or B may also be crystalized and/or otherwise isolated. Compositions, including pharmaceutical compositions, can then be made, including one or both of Polymorphs A or B.

BRIEF DESCRIPTION OF DRAWINGS

This application/patent contains at least one drawing executed in color.

The foregoing summary and the following detailed description are better understood when read in conjunction with the appended drawings. Example embodiments are shown in the drawings; however, it is understood that the embodiments are not limited to the specific structures depicted herein. In the drawings:

FIGS. 4A and 4B are X-Ray Powder Diffraction (XRPD) outputs comparing taurolidine Polymorphs A and B, according to an example embodiment of the present disclosure.

DETAILED DESCRIPTION

The terminology used in the present disclosure is for the purpose of describing particular example embodiments only and is not intended to be limiting. As used in the description of the embodiments of the disclosure and the appended claims, the singular forms "a," "an," and "the" are intended to include the plural forms as well, unless the context clearly indicates otherwise.

The term "and/or," as used herein, refers to and encompasses any and all possible combinations of one or more of the associated listed items.

The term "about," as used herein when referring to a measurable value such as an amount of a component, time, temperature, and the like, is meant to encompass variations of 20%, 10%, 5%, 1%, 0.5%, or even 0.1% of the specified amount. Unless otherwise defined, all terms, including technical and scientific terms used in the description, have the same meaning as commonly understood by one of ordinary skill in the art to which this disclosure belongs.

Improved Synthesis of Taurolidine

Taurolidine can be synthesized according to the following (the "Conventional Synthesis"):

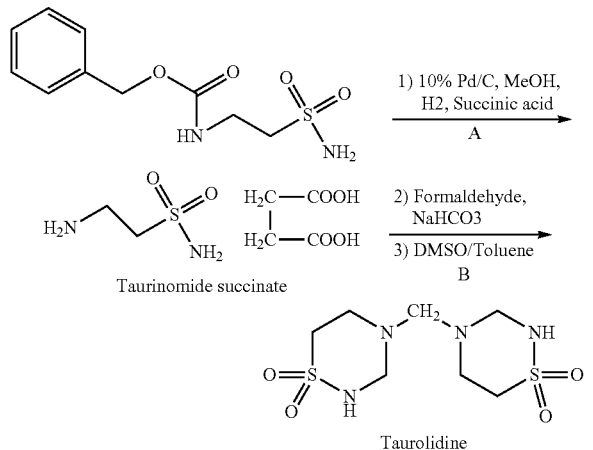

Step A of the Conventional Synthesis includes catalytic hydrogenation (Step A) of Cbz-taurinamide using palladium on carbon and succinic acid. Step B comprises condensation of the taurinamide-acid material to form taurolidine using toluene and dimethylsulfoxide (DMSO), both classified as Class 2 solvents. The use of a Class 2 solvent, such as toluene in the Conventional Synthesis, can result in high or undesirable levels of impurities. The Conventional Synthesis can also result in a high or undesirable level of taurultam and/or taurinamide.

In an embodiment, the disclosure provides a synthesis of, or method of manufacturing, taurolidine. The synthesis of, or method of manufacturing, taurolidine includes the following steps:

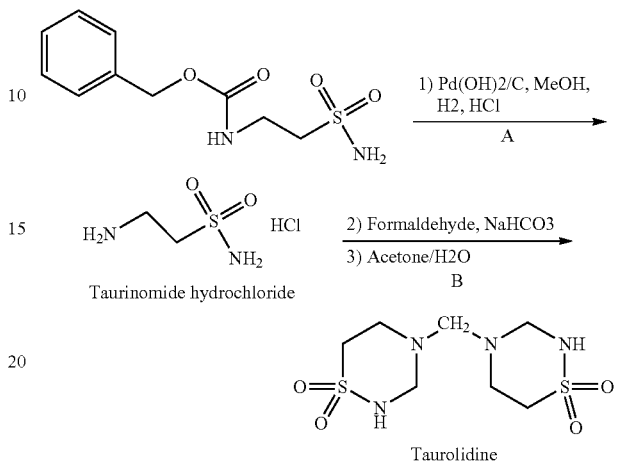

Improved Purity Profile

The synthesis of this disclosure includes catalytic hydrogenation (Step A) of Cbz-taurinamide using Pearlman's catalyst (i.e., $Pd(OH)_2$) and Hydrochloric acid. Step B includes condensation of the taurinamide-acid material to form taurolidine using acetone (a Class 3 solvent) and water. The effect or improvement of using Pearlman's catalyst and Hydrochloric acid in Step A instead of Palladium on carbon and succinic acid in the Conventional Synthesis may be demonstrated via efficiency or rate of removal of the N-carboxybenzyl (Cbz) group to form a taurinamide-acid intermediate. The synthesis of this disclosure provides a cleaner reaction using a Class 3 solvent, e.g., acetone, in the purification process.

Figure 5:
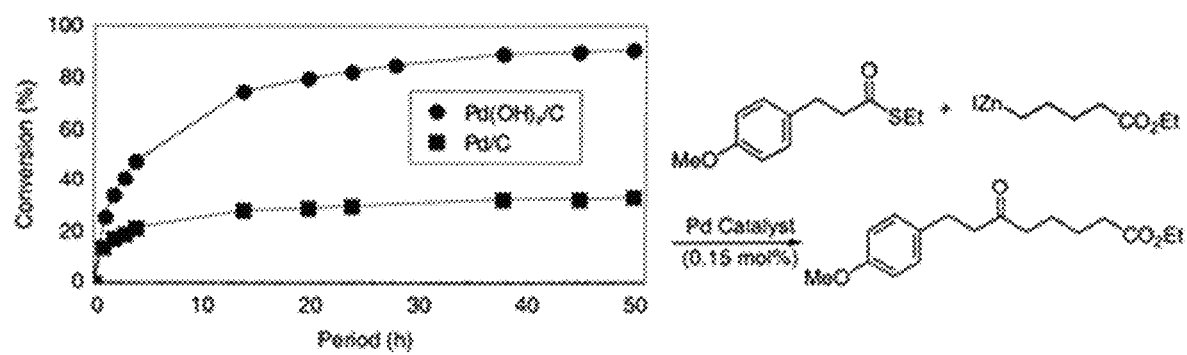
FIG. 5 is a graph showing the effect of Perlman's catalyst on the yield and speed of reaction, according to an example embodiment of the present disclosure.

A traditional catalytic hydrogenation approach used is Pd/C, H2 (high pressure). The present disclosure provides the discovery that Perlman's catalyst accelerates the speed of the reaction and increases the yield of the reaction. (See FIG. 5). In the synthesis of the present disclosure, HCl is used because the starting material for Taurolidine is the hydrochloric acid salt of Taurinamide. Traditional synthesis of Taurolidine uses Pd/C when very stable protection groups are inserted to a molecular structure to further synthesis and prevent unwanted side reactions at the protected site. Hydrogenation reactions involving Pd/C to remove the protection group may proceed at slower rates than those using Pearlman's catalyst and with lower yields. Also, side reactions may produce by-products and impurities. In the case of the carboxybenzyl carbamate (Cbz-N) protecting group, hydrogenolysis could result in the formation of benzyl alcohol and toluene as by-products in addition to Taurinamide succinate. Hydrogenolysis with Pd/C may be strongly affected by the nature of the solvent, with this ascending order of efficiency: Toluene<Methanol<Ethanol <Tetrahydrofuran. The synthesis of the present disclosure can use Hydrochloric acid, which is stronger than succinic acid used in the Conventional Synthesis, facilitating debenzylation process via protonation of the oxygen atom of the O-benzyl ether protection group.

Residual Organic Solvents: USP (c467) and ICH (Q3C, R8) Classification

Residual organic solvents can be Class 1, Class 2 or Class 3, as set forth below:

Class 1 (USP c467) solvents should not be employed in the manufacture of drug substances, excipients, and drug products because of the unacceptable toxicities or deleterious environmental effects of these residual solvents. According to the ICH Q3C guidelines, Class 1 solvents may comprise known human carcinogens, strongly suspected human carcinogens, and environmental hazards.

Class 2 (USP c467) Class 2 solvents should be limited in drug substances, excipients, and drug products because of the inherent toxicities of the residual solvents. According to the ICH Q3C guidelines, Class 2 solvents may be suspected of other significant toxicities.

Class 3 (USP c4367) May be regarded as less toxic and of lower risk to human health. According to the ICH Q3C guidelines, Class 3 solvents may comprise solvents with low toxic potential to man; no health-based exposure limit is needed. Class 3 solvents may have PDEs of 50 mg or more per day.

thesized according to the Present Synthesis can have a better purity profile and/or have lower levels of related impurities (e.g., Taurine and Taurultam) than the taurolidine synthesized according to the Conventional Synthesis. In an embodiment, taurolidine synthesized according to the Present Synthesis can have a better purity profile than taurolidine synthesized according to the Conventional Synthesis. Taurolidine synthesized according to the Conventional Synthesis may have higher levels of Taurultam and may contain taurinamide while taurolidine synthesized according to the Present Synthesis may not contain taurinamide. Taurolidine synthesized according to the Conventional Synthesis may use Class 2 solvents in the active pharmaceutical ingredient (API) formulation step and may exhibit additional carry-over residual solvents, while taurolidine synthesized according to the Present Synthesis may use a Class 3 solvent (e.g., acetone), which has a lower toxicity and poses a lower risk to human health than the Class 2 solvents (e.g., toluene and hexane).

Table 2 below sets forth a comparison of certain impurities and residual solvents of a taurolidine API synthesized according to Conventional Synthesis and a taurolidine API synthesized according to Present Synthesis.

TABLE 2

| Test | MFG Date Specification | Taurolidine API synthesized according to Conventional Synthesis | | | Taurolidine API synthesized according to the Present Synthesis | | | |
|---|---|---|---|---|---|---|---|---|
| | Lot No. | TAU/3/001/10 September 2010 Result | TAU/3/002/10 September 2010 Result | TAU/3/002/10 September 2010 Result | Lot No. MFG Date Specification | FP-000417 28 May 2016 Result | FP-000429 10 Jul. 2016 Result | FP-000528 8 Dec. 2016 Result |
| Potency (HPLC Assay) | 95.0-101.0% | 98.6 | 98.4 | 98.6 | 95.0-103.0% | 101.1 | 101.2 | 98.3 |
| Impurities | | | | | | | | |
| Taurultam content | NMT 5.0% | 0.9 | 1.5 | 0.9 | NMT 5% | 0.4 | 0.4 | 1.0 |
| Taurine | NMT 0.2% | 0.01 | ND | ND | NMT 0.2% | ND | ND | ND |
| Taurinamide | NMT 0.5% | 0.24 | 0.18 | 0.19 | N/A | N/A | N/A | N/A |
| Individual unknown impurities | NMT 0.10% | 0.05 | 0.06 | 0.06 | NMT 0.1% | ND | ND | ND |
| Total impurities | NMT 3.0% | 0.4 | 0.3 | 0.3 | NMT 3% | ND | ND | ND |
| Residual solvents, ICH Q3C (R8) | | | | | | | | |
| Acetone | NMT 5000 ppm | N/A | N/A | N/A | NMT 5000 ppm | <1000 | <1000 | <1000 |
| Methanol | NMT 3000 ppm | 61 | 269 | 278 | NMT 3000 ppm | <600 | <600 | <600 |
| n-Hexane | NMT 290 ppm | 2 | ND | ND | N/A | N/A | N/A | N/A |
| Toluene | NMT 890 ppm | ND | 27 | 27 | N/A | N/A | N/A | N/A |
| Ethyl acetate | NMT 5000 ppm | 1 | ND | ND | N/A | N/A | N/A | N/A |
| DMSO | NMT 5000 ppm | 2197 | 3049 | 3244 | N/A | N/A | N/A | N/A |

Table 1 below compares various residual solvents used in, or carried over from a precursor in, the Conventional Synthesis and the Present Synthesis based on class.

TABLE 1

| CLASS | RESIDUAL SOLVENTS USED in RXN or CARRIED OVER from PRECURSOR | Conventional Synthesis | Present Synthesis |
|---|---|---|---|
| 2 | Toluene | Yes | No |
| | Hexane | Yes | No |
| 3 | Acetone | No | Yes |
| | Dimethylsulfoxide (DMSO) | Yes | No |
| | Ethyl acetate | Yes | Yes |
| | Methanol | Yes | No |

In an embodiment, the taurolidine synthesized according to the Present Synthesis can be free of, substantially free of, or can have low levels of impurities. The taurolidine syn- Although USP classifies Dimethyl sulfoxide (DMSO) as a Class 3 solvent, it is possible that DMSO could have an organotropic action of the solvent directing the carcinogenic effect of nitrosamines. If patients are receiving certain class of medications for hypertension, nitrosamines may be of concern to the FDA and DMSO may enhance the carcinogenic effect.

The present disclosure also provides an advantageous analytical method applied for detecting impurities in the Taurolidine according to the present disclosure. A traditional analytical technique for testing APIs is HPLC coupled with UV/Visible detector, which has limitation detecting impurities whenever their chemical structures do not have chromophores (i.e., UV/Vis light absorbing chemical structural moiety). The confirmation of reduced, limited, or zero impurities for the Present Synthesis can be performed through HPLC-CAD (Charged Aerosol Detection) which is independent of chromophores because it is based the detection of particles charged with an ion-jet and detects impurities at the nanogram level.

Polymorphs

In an embodiment, one or more polymorphs of taurolidine synthesized according to the Present Synthesis is provided, for example, Polymorph A and/or Polymorph B. Differential Scanning Calorimetry (DSC) and XRPD were used to characterize two polymorphic crystalline structures of taurolidine synthesized according to the Present Synthesis. In view of the present synthesis of taurolidine detailed above, the polymorphs, when purified, crystallized or otherwise isolated for later use, are free of, substantially free of, or have low levels of at least Class 2 impurities such as hexane and toluene. In an embodiment, one or more polymorphs of taurolidine synthesized according to the Present Synthesis is provided, for example, Polymorph A and/or Polymorph B, which are free of Class 2 impurities such as hexane and toluene.

Figure 1:
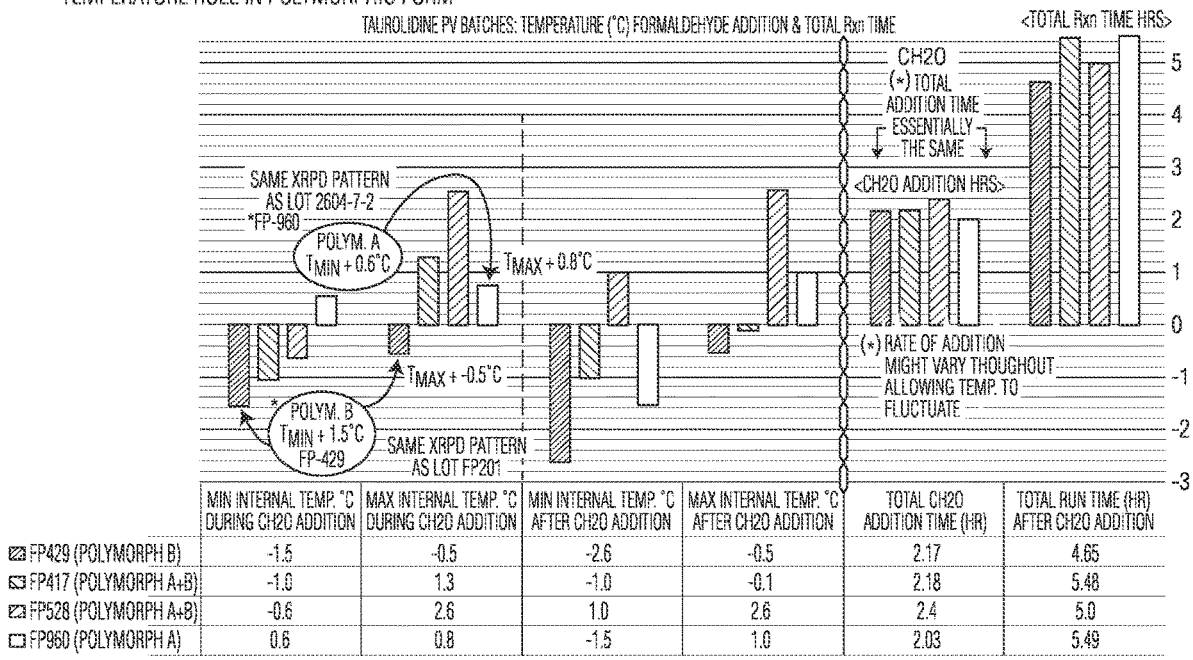
FIG. 1 is a chart showing the role of temperature in various polymorph forms of a taurolidine compound, according to an example embodiment of the present disclosure.

FIG. 1 is a chart showing the role of temperature in various polymorph forms of a taurolidine compound, according to an example embodiment of the present disclosure. Control of the temperature of the reaction mixture during the addition of reagents may be important for controlling the polymorphic content (see FIG. 1). In an embodiment, control of the temperature of the reaction mixture during the addition of reagents is important for controlling the polymorphic content. In an embodiment, a lower temperature of the reaction mixture can produce Polymorph B. In an embodiment, a higher temperature of the reaction mixture can produce Polymorph A.

Figure 2:
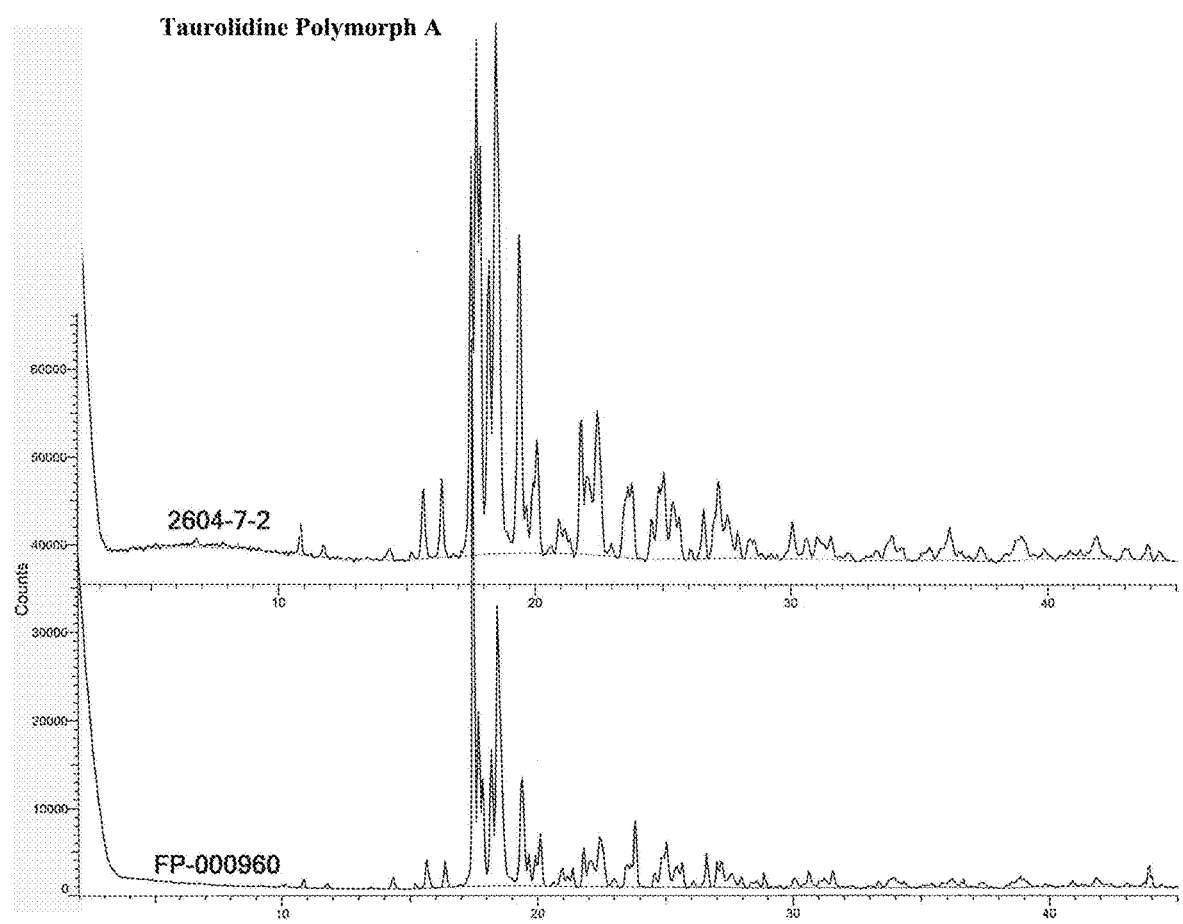
FIG. 2 is an X-Ray Powder Diffraction (XRPD) output of a taurolidine Polymorph A, according to an example embodiment of the present disclosure.

FIG. 2 is an X-Ray Powder Diffraction (XRPD) output of a taurolidine Polymorph A, according to an example embodiment of the present disclosure. Lower temperature (e.g., $-1.5°$ C. to $-0.5°$ C.) may favor the kinetic Polymorph B (see FIG. 2, an XRPD for pure Polymorph B).

Figure 3:
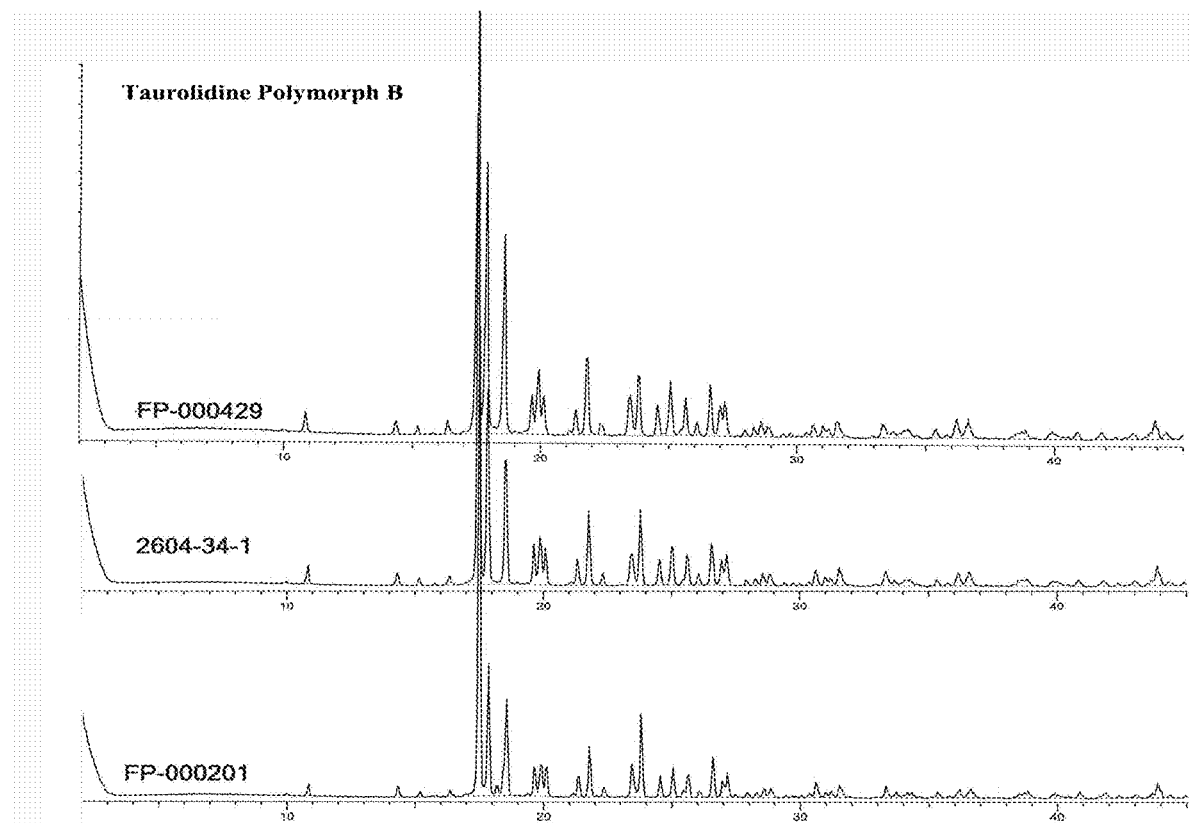
FIG. 3 is an X-Ray Powder Diffraction (XRPD) output of a taurolidine Polymorph B, according to an example embodiment of the present disclosure.

FIG. 3 is an X-Ray Powder Diffraction (XRPD) output of a taurolidine Polymorph B, according to an example embodiment of the present disclosure. Higher temperatures (e.g., $0°$ C.-$5°$ C.) may favor the thermodynamic Polymorph A (see FIG. 3, an XRPD for pure Polymorph A).

FIGS. 4A and 4B are X-Ray Powder Diffraction (XRPD) outputs comparing taurolidine Polymorphs A and B synthesized according to the Present Synthesis, according to an example embodiment of the present disclosure. A study (Alcami Report SS19-032-RHL-190128) confirmed taurolidine Polymorph B (see FIG. 4).

Taurolidine Polymorphs A and B synthesized according to the Present Synthesis may both be soluble in 26.1 mg/mL aqueous citric acid, at $T=25°$ C.

Formulations

U.S. Pat. No. 7,696,182 titled "Antimicrobial Locking Solutions Comprising taurinamide Derivatives and Biologically Acceptable Salts and Acids, with the Addition of Small Concentrations of Heparin" is incorporated herein by reference in the entirety, except to the extent that the incorporated material is inconsistent with the express disclosure herein, in which case the language in this disclosure controls.

The following disclosure may relate to taurolidine synthesized according to the Present Disclosure. The taurolidine may be free of impurities, substantially free of impurities or may have low levels of impurities. The taurolidine may be in the form of Polymorph A and/or Polymorph B as disclosed herein. In an embodiment, taurolidine based antimicrobial and anti-coagulant lock solutions may be made with the polymorphs described herein, which reduce catheter patency complications brought on by taurolidine reacting with red cells and the characteristics of the clot formed in the distal portion of a catheter.

The concentration of taurolidine in such solutions is preferably in the range of from about 0.4 to about 5% by weight, depending upon the solubility of the compound. The addition of citrates and citric acid in combination, or alternatively the addition of citric acid and adjustment of the pH with sodium hydroxide, such that the pH of the end solution is in the vicinity of 5.2 to 6.5, substantially increases the biocidal effectiveness of taurolidine solution. The approach creates a buffer system of citric acid/sodium citrate by adjustment of pH using sodium hydroxide.

Thus, the use of citric acid and sodium citrate in this combination thus increases the stability and solubility of taurolidine in solution and prevents or severely slows down the precipitation out of solid taurolidine and reaction products frequently seen in taurolidine solution prepared with polyvinylpyrrolidone (PVP). Long term stability tests have verified this result. The composition employed in the practice of the present invention preferably also contains a pharmacologically acceptable carrier solution, such as, water for injection.

Other biologically acceptable acids and biologically acceptable salts thereof are possible for combination with taurolidine. Other possible such acids are acetic acid, dihydroacetic acid, benzoic acid, citric acid, sorbic acid, propionic acid, oxalic acid, fumaric acid, maleic acid, hydrochloric acid, malic acid, phosphoric acid, sulfurous acid, vanillic acid, tartaric acid, ascorbic acid, boric acid, lactic acid, ethylenediaminetetraacetic acid (EDTA), ethylene glycol-bis-{β-aminoethyl ether}-N,N,N',N'-tetraacetic acid, and diethylenetriamine pentaacetic acid, esters of p-hydroxybenzoic acid (Parabens), and the like, and biologically acceptable salts of the foregoing, such as, ammonium phosphate, potassium citrate, potassium metaphosphate, sodium acetate, sodium citrate, sodium lactate, sodium phosphate, and the like. A blood anticoagulating amount of an acid selected from the group consisting of citric acid, phosphoric acid, ethylenediaminetetraacetic acid (EDTA), ethylene glycol-bis-{β-aminoethyl ether}-N,N,N',N'-tetraacetic acid, and diethylenetriamine pentaacetic acid and biologically acceptable salts thereof is preferred. It is preferred that the acid employed in the practice of the present invention be an organic acid, especially one having at least one carboxyl group, particularly citric acid or EDTA. It is more preferred that the acid be citric acid and most preferred that it be used in combination with a citrate salt, e.g., sodium citrate, since, in addition to its pH lowering and anticoagulation capabilities, it is also known to be an antiseptic at the 3% level.

Since calcium is one factor that is known to have a role in the coagulation of blood, it is believed possible that at least part of EDTA's efficacy in anticoagulant activity may be brought about by this means. Sodium citrate is also believed to have anticoagulation properties by virtue of its ability to generate insoluble calcium citrate.

In an embodiment, the present disclosure provides a formulation that includes taurolidine synthesized according to the Present Disclosure. The taurolidine may be free of impurities, substantially free of impurities or may have low levels of impurities. The taurolidine may be in the form of Polymorph A and/or Polymorph B as disclosed herein. Table 3 below sets forth a formulation, according to an embodiment of the present disclosure. NaOH may be used at early stage raise pH to between 5.9-6.1. Final pH range of the citrate buffered system may be 5.5-6.5.

TABLE 3

| MATERIAL USED FOR DRUG COMPOUNDING | FUNCTION | QUANTITY (350 L BATCH SIZE) | CONCENTRATION |
|---|---|---|---|
| Heparin sodium | Anticoagulant | 1,750 g | 1000 Units/mL[(1)] |
| Taurolidine | Antimicrobial | 4,725 g | 13.50 mg/mL |
| Citric acid anhydrous | Buffer system | 9,135 g | 26.10 mg/mL |
| Water for injection | Solvent | q.s. ad 350 L | NA |

LMWH Heparin

As noted above, the formulation can further comprise LMWH Heparin. The following may be advantages of using LMWH Heparin in such formulation: the formulation may require only once or twice daily dosing, may not require monitoring activated partial thromboplastin time (aPTT), lower risk of bleeding Heparin-induced thrombocytopenia (low platelet counts may cause bleeding), lower risk of osteoporosis, and/or anticoagulant effect of UH can be reverted with protamine sulfate, but its effect on LMWH may be limited.

Buffering System

In an embodiment, formulations of the present disclosure can comprise alternative buffering systems with pH capacity that offer better and/or comparable taurolidine solubility profile as well as safety profile as existing formulations. Existing buffers in parenteral products can be citrate (Neutrolin, for example), phosphate and acetate, which are already approved by the FDA. Other buffering systems are listed in Table 4 below.

TABLE 4

| | | | pH Shift during Freezing | |
|---|---|---|---|---|
| Buffer Reagent | pKa | Buffering Range | pH @ 25° C. | ΔpH @ −20° C. |
| Phosphoric acid | 2.1, 7.2, 12.3 | Neutral - Basic | 7.2 | −1.8 |
| Citric acid | 3.1, 4.8, 6.4 | Acidic - Neutral | 6.2 | −0.2 |
| Acetic acid | 4.8 | Acidic | 5.6 | +0.5 |
| Histidine | 1.8, 6.1, 9.2 | Neutral | 5.4 | +0.8 |
| Lactic acid | 3.9 | Acidic | N/A | N/A |
| Tromethamine | 8.1 | Neutral - Basic | 7.2 | +2.1 |
| Gluconic acid | 3.6 | Acidic | N/A | N/A |
| Aspartic acid | 2.1, 3.9, 9.8 | Acidic | N/A | N/A |
| Glutamic acid | 2.1, 4.1, 9.5 | Acidic | N/A | N/A |
| Tartaric acid | 3.2, 4.9 | Acidic | 5.0 | −0.3 |
| Succinic acid | 4.2, 5.6 | Acidic - Neutral | 5.6 | +0.3 |
| Malic acid | 3.4, 5.1 | Acidic - Neutral | 5.0 | −0.3 |
| Fumaric acid | 3.0, 4.4 | Acidic | N/A | N/A |
| α-Ketoglutaric | 2.5, 4.7 | Acidic - Neutral | N/A | N/A |

Conclusion

While the present disclosure has been discussed in terms of certain embodiments, it should be appreciated that the present disclosure is not so limited. The embodiments are explained herein by way of example, and there are numerous modifications, variations and other embodiments that may be employed that would still be within the scope of the present disclosure.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. The examples set forth in this document are for illustrative purposes and all elements of the example may not be required or exhaustive. Accordingly, other implementations are within the scope of the following claims. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter. For example, the steps and/or limitations in the specification, drawings, and/or claims may be performed in an order other than the order set forth in the specification, drawings, and/or claims.

In addition, it should be understood that any figures which highlight the functionality and advantages are presented for example purposes only. The disclosed methodology and system are each sufficiently flexible and configurable such that they may be utilized in ways other than that shown. For example, other steps may be provided, or steps may be eliminated, from the described flows, and other components may be added to, or removed from, the described systems.

Although the term "at least one" may often be used in the specification, claims and drawings, the terms "a", "an", "the", "said", etc. also signify "at least one" or "the at least one" in the specification, claims and drawings.

Finally, it is the applicant's intent that only claims that include the express language "means for" or "step for" be interpreted under 35 U.S.C. 112(f). Claims that do not expressly include the phrase "means for" or "step for" are not to be interpreted under 35 U.S.C. 112(f).

The invention claimed is:

1. A locking solution composition for treating and reducing infection and flow reduction in blood catheters, wherein the composition comprises a solution of:
 a. taurolidine, wherein all or substantially all of the taurolidine was obtained from a polymorph of the taurolidine, wherein the polymorph is Polymorph A characterized by an X-ray powder diffraction (XRPD) plot shown in FIG. 2;
 b. a biologically acceptable acid; and
 c. low concentration heparin, in a concentration of 50 to 2500 units per mL of the composition.

2. The composition of claim 1, wherein the composition is completely free from hexane and toluene.

3. The composition of claim 1 wherein the biologically acceptable acid is chosen from the group consisting of citric acid and lactic acid.

4. The composition of claim 1 wherein low concentration heparin is in the range of 50 to 1750 units per mL.

5. The composition of claim 1 wherein low concentration heparin is in the range of 50 to 500 units per mL.

6. The composition of claim 1 wherein the low concentration heparin is in the range 50 to 150 units per mL.

7. The composition of claim 1, wherein the heparin is low molecular weight (LMW) heparin.

8. A locking solution composition for treating and reducing infection and flow reduction in blood catheters, wherein the composition comprises a solution of:

a. taurolidine, wherein all or substantially all of the taurolidine was obtained from a polymorph of the taurolidine, wherein the polymorph is Polymorph B characterized by an X-ray powder diffraction (XRPD) plot shown in FIG. 3;

b. a biologically acceptable acid; and c. low concentration heparin, in a concentration of 50 to 2500 units per mL of the composition.

9. The composition of claim 8, wherein the composition is completely free from hexane and toluene.

10. The composition of claim 8 wherein the biologically acceptable acid is chosen from the group consisting of citric acid and lactic acid.

11. The composition of claim 8 wherein low concentration heparin is in the range of 50 to 1750 units per mL.

12. The composition of claim 8 wherein low concentration heparin is in the range of 50 to 500 units per mL.

13. The composition of claim 8 wherein the low concentration heparin is in the range 50 to 150 units per mL.

14. The composition of claim 8, wherein the heparin is low molecular weight (LMW) heparin.

15. A locking solution composition for treating and reducing infection and flow reduction in blood catheters, wherein the composition comprises a solution of:

a. taurolidine, wherein all or substantially all of the taurolidine was obtained from polymorphs of the taurolidine, wherein the polymorphs are Polymorph A characterized by an X-ray powder diffraction (XRPD) plot show in FIG. 2 and Polymorph B characterized by an X-ray powder diffraction (XRPD) plots shown in FIG. 3;

b. a biologically acceptable acid; and c. low concentration heparin, in a concentration of 50 to 2500 units per mL of the composition.

16. The composition of claim 15, wherein the composition is completely free from hexane and toluene.

17. The composition of claim 15 wherein the biologically acceptable acid is chosen from the group consisting of citric acid and lactic acid.

18. The composition of claim 15 wherein low concentration heparin is in the range of 50 to 1750 units per mL.

19. The composition of claim 15 wherein low concentration heparin is in the range of 50 to 500 units per mL.

20. The composition of claim 15 wherein the low concentration heparin is in the range 50 to 150 units per mL.

21. The composition of claim 15, wherein the heparin is low molecular weight (LMW) heparin.

22. A locking solution composition for treating and reducing infection and flow reduction in blood catheters, wherein the composition comprises a solution of:

a. taurolidine, wherein all or substantially all of the taurolidine was obtained from one or more polymorphs of the taurolidine, wherein the one or more polymorphs are selected from the group consisting of Polymorph A characterized by an X-ray powder diffraction (XRPD) plot shown in FIG. 2 and Polymorph B characterized by an X-ray powder diffraction (XRPD) plot shown in FIG. 3; and b. a biologically acceptable acid.

23. The composition of claim 22, wherein the composition is completely free from hexane and toluene.

24. The composition of claim 22, wherein the biologically acceptable acid is chosen from the group consisting of citric acid and lactic acid.

* * * * *